(12) United States Patent
Laubert et al.

(10) Patent No.: US 8,377,139 B2
(45) Date of Patent: Feb. 19, 2013

(54) STANDALONE INTERBODY FUSION DEVICE WITH LOCKING AND RELEASE MECHANISM

(75) Inventors: Nikolay Laubert, Allentown, PA (US); Charles Wing, Center Valley, PA (US)

(73) Assignee: Aesculap Implant Systems, LLC, Center Valley, PA (US)

( * ) Notice: Subject to any disclaimer, the term of this patent is extended or adjusted under 35 U.S.C. 154(b) by 258 days.

(21) Appl. No.: 12/817,778

(22) Filed: Jun. 17, 2010

(65) Prior Publication Data

US 2011/0313528 A1 Dec. 22, 2011

(51) Int. Cl.
A61F 2/44 (2006.01)

(52) U.S. Cl. ........... 623/17.16; 606/246; 606/305

(58) Field of Classification Search .......... 411/166; 606/249, 279, 289, 291, 305, 246; 623/17.11, 623/17.16
See application file for complete search history.

(56) References Cited

U.S. PATENT DOCUMENTS

| | | | |
|---|---|---|---|
| 2,376,089 A * | 5/1945 | Savageau | 411/81 |
| 5,520,690 A | 5/1996 | Errico | |
| 5,554,191 A | 9/1996 | Lahille | |
| 5,578,034 A | 11/1996 | Estes | |
| 5,888,223 A | 3/1999 | Bray, Jr. | |
| 5,954,722 A | 9/1999 | Bono | |
| 6,206,881 B1 | 3/2001 | Frigg et al. | |
| 6,261,291 B1 | 7/2001 | Talaber | |
| 6,342,074 B1 | 1/2002 | Simpson | |
| 6,485,517 B1 | 11/2002 | Michelson | |
| 6,579,290 B1 | 6/2003 | Hardcastle | |
| 6,626,907 B2 | 9/2003 | Campbell et al. | |
| 6,629,998 B1 * | 10/2003 | Lin | 623/17.11 |
| 6,716,214 B1 | 4/2004 | Jackson | |
| 6,730,127 B2 | 5/2004 | Michelson | |
| 6,896,676 B2 | 5/2005 | Zubot | |
| 6,899,735 B2 | 5/2005 | Coates | |
| 6,972,019 B2 | 12/2005 | Michelson | |
| 6,974,461 B1 | 12/2005 | Wolter | |
| 7,077,864 B2 | 7/2006 | Byrd, III | |
| 7,172,627 B2 | 2/2007 | Fiere | |
| 7,229,443 B2 | 6/2007 | Eberlein | |
| 7,232,464 B2 | 6/2007 | Mathieu | |
| 7,288,095 B2 | 10/2007 | Baynahm | |
| 7,318,825 B2 | 1/2008 | Butler | |
| 7,468,069 B2 | 12/2008 | Baynham | |
| 7,481,829 B2 | 1/2009 | Baynham | |
| 7,618,456 B2 | 11/2009 | Mathieu et al. | |
| 7,658,739 B2 | 2/2010 | Shluzas | |
| 7,662,174 B2 | 2/2010 | Doubler | |
| 7,678,113 B2 | 3/2010 | Melkent | |
| 7,704,250 B2 | 4/2010 | Michelson | |
| 7,704,279 B2 | 4/2010 | Moskowitz | |

(Continued)

*Primary Examiner* — Kevin T Truong
*Assistant Examiner* — Larry E Waggle, Jr.
(74) *Attorney, Agent, or Firm* — RatnerPrestia

(57) ABSTRACT

An implantable assembly includes an anchor member and a spacer. The anchor member has a hub portion and a shank portion. The spacer includes a central opening to receive bone fusion material and at least one passage for receiving the anchor member. In one embodiment, the passage includes first and second means for locking the anchor member in the passage against backout. The second means for locking the anchor member in the passage against backout includes means for centering the anchor member in the passage and means for stabilizing the anchor member in the passage. In addition, the second means for locking the anchor member in the passage against backout provides a mechanical advantage to assist in driving the screw into bone and mechanical advantage to assist in reversing the screw out of the spacer.

20 Claims, 6 Drawing Sheets

U.S. PATENT DOCUMENTS

| | | |
|---|---|---|
| 2005/0049593 A1 | 3/2005 | Duong |
| 2005/0071010 A1 | 3/2005 | Crozet |
| 2005/0177240 A1 | 8/2005 | Blain |
| 2005/0216081 A1 | 9/2005 | Taylor |
| 2006/0085071 A1 | 4/2006 | Lechmann et al. |
| 2006/0155285 A1 | 7/2006 | Anderson |
| 2008/0167721 A1 | 7/2008 | Boa |
| 2008/0183293 A1 | 7/2008 | Parry |
| 2008/0243192 A1 | 10/2008 | Jacene |
| 2008/0249569 A1 | 10/2008 | Waugh |
| 2008/0249575 A1 | 10/2008 | Waugh |
| 2008/0269806 A1 | 10/2008 | Zhang |
| 2008/0281425 A1 | 11/2008 | Thalgott |
| 2008/0294260 A1 | 11/2008 | Gray |
| 2008/0300685 A1 | 12/2008 | Carls |
| 2008/0306596 A1 | 12/2008 | Jones |
| 2009/0024170 A1 | 1/2009 | Kirschman |
| 2009/0030520 A1* | 1/2009 | Biedermann et al. ...... 623/17.16 |
| 2009/0088808 A1 | 4/2009 | Lindemann et al. |
| 2009/0270927 A1* | 10/2009 | Perrow et al. ................. 606/286 |
| 2010/0010547 A1 | 1/2010 | Beaurain |
| 2010/0036423 A1 | 2/2010 | Hayes |
| 2010/0049324 A1 | 2/2010 | Valdevit |
| 2010/0057205 A1 | 3/2010 | Justin |
| 2010/0057206 A1 | 3/2010 | Duffield |
| 2010/0063545 A1 | 3/2010 | Richelsoph |
| 2010/0070037 A1 | 3/2010 | Parry |
| 2010/0087925 A1 | 4/2010 | Kostuik et al. |
| 2010/0094348 A1 | 4/2010 | Biedermann |
| 2010/0106249 A1 | 4/2010 | Tyber |
| 2010/0125333 A1 | 5/2010 | Zdeblick |
| 2010/0131017 A1 | 5/2010 | Farris |

* cited by examiner

STANDALONE INTERBODY FUSION DEVICE WITH LOCKING AND RELEASE MECHANISM

FIELD

This disclosure relates generally to implantable assemblies used for spinal fusion, and more particularly to standalone interbody fusion devices with mechanisms that lock anchor members against backout, unlock anchor members to facilitate their removal, guide anchor members during insertion and/or stabilize anchor members in fusion devices.

BACKGROUND

Spinal discs provide support between adjacent vertebrae in a spinal column. Over time, discs can rupture, degenerate or protrude outside of their normal space as a result of injury, degradation or disease. In such cases, the condition of the disc can be weakened or compromised to the point that the intervertebral space around the disc collapses. Changes in disc shape can cause the spine to lose its normal curvature, create impingement of nerves in the disc space, and result in chronic back pain.

A number of surgical procedures can be performed to treat damaged discs. In one procedure, the degenerative disc is removed, and the remaining adjacent vertebrae are connected by fusion. This procedure may involve the use of an intervertebral body spacer or cage in conjunction with bone graft material. The spacer is inserted between the vertebrae to create and maintain a desired spacing between the vertebrae. The bone graft material promotes fusion of the vertebrae for long term stability. During the fusion process, it is desirable to inhibit relative movement of the spacer and adjacent vertebrae. To this end, many spacers are provided with anchor members, such as bone screws, that are inserted through the spacer and into the vertebrae to stabilize the spacer between the vertebrae.

Anchor members that secure spacers between vertebrae can loosen over time in response to micro motion and other factors. Once anchor members are loosened, they may back out of the vertebrae and no longer hold the spacer in a stable condition. In addition, loosened anchor members can project from the vertebral space and contact tissue, blood vessels or organs, causing damage.

There have been a number of attempts to reduce the occurrence of screw backout. For example, U.S. Pub. No. 2008/0249569 describes implants with face plates that are attachable over the implants to inhibit anchors from backing out of the implants. In one embodiment, the implant has anchor apertures that pass through the front surface of the implant. The side surfaces of the implant include recesses with attachment features that connect with attachment features on the face plate. The face plate is attachable over the front surface of the implant to cover the anchor apertures. In this position, the faceplate inhibits the anchor members from backing out of the implant. The faceplate is attached over the implant once the implant is inserted into the vertebral space, and after the anchor members are driven into the vertebrae.

U.S. Pub. No. 2006/0085071 discloses another spacer with bone screws that have male threads on the screw heads. The screws are inserted through a front plate that has bore holes. The bore holes have short threaded sections at the entrances of the bore holes which mate with the screw heads. According to the inventors, the threaded engagement anchors the screws in the front plate in a rigid manner. After the screws are anchored in the front plate, a separate securing plate is attached over the bore holes and screws to inhibit the screws from backing out of the spacer.

U.S. Pub. No. 2008/0249575 discloses interbody spacers with deformable locking rings to inhibit bone screws from backing out of the screw passages. In general, the locking rings deflect radially to allow the bone screws to advance into the passage to a certain point. Once the bone screws pass through the locking rings, the locking rings return to a relaxed configuration that traps the bone screws in the passages and inhibits the screws from backing out. The screw passages are relatively short and appear to engage only a small portion of the screw heads.

U.S. Pub. No. 2009/0030520 discloses an interbody spacer with bone screws having a special thread configuration. Each bone screw has a head and a shaft with two sections. The shaft includes an external thread at one section and a clearance groove at another section that separates the external thread from the head. The external thread is designed to engage an internal thread inside the screw passage in the spacer, and then disengage from the internal thread as the screw is advanced into the bone. Once the screw is fully seated in the spacer, the external thread portion disengages from the internal thread in the spacer, and the clearance groove is aligned with the internal thread. The bone screw is then rotated another 90°-270° in the seated position to separate the orientation of the external thread from the internal thread runout. Because the external thread is rotationally separated and disengaged from the internal thread, the external thread abuts an end face on the spacer, preventing the screw from backing out through the passage.

One drawback to known designs is that they provide no mechanism to assist removal of the bone screw from the spacer. A bone screw may need to be removed for a number of reasons. For example, the bone screw and spacer may need to be removed where the patient's condition changes or where the surgeon decides that the bone screw needs to be replaced with a shorter or longer screw. Removing the bone screw is almost impossible if there is no mechanism to get the screw out of the bone and out of the spacer. This is particularly true with designs that trap the head of the screw behind a locking ring or other obstruction inside the spacer, as shown for example in U.S. Pub. No. 2008/0249575. Locking rings are typically designed to permanently trap the screw head in the spacer behind the locking ring. Even in designs where the screw head is unobstructed, the typical design still provides no mechanism to help remove the screw out of the passage. In U.S. Pub. No. 2009/0030520, for example, the bone screw is driven into bone and rotated until its external thread misaligns with the internal thread in the spacer. The external thread abuts the end face of the spacer and cannot be reengaged with the internal thread to remove the screw. Moreover, the screw head is countersunk in the screw passage, providing no way to grab onto the head and apply axial force on the head to remove the screw.

Another drawback to many known designs is that the spacer provides no control against overtightening of bone screws. Typically, a screw hole is tapped and/or pre-drilled into the bone. As a bone screw is driven into the hole in the bone, a delicate thread is formed in the interior of the hole that mates with the thread on the screw. The delicate thread in the bone will be damaged and stripped if the screw is overtightened, When the thread in the bone is stripped, the thread can no longer assist in removing the screw in the event the screw is unscrewed from the bone. Many known spacers lack a positive stop mechanism to limit rotation of the screw and prevent overtightening and stripping of the bone thread. In U.S. Pub. No. 2009/0030520, for example, the screw is intended to be rotated through some unspecified angle after it is seated in the spacer to create a compression lock. The screw is intended to be rotated after it is seated to misalign the external thread on the shaft and internal thread in the passage. Spacers of this kind do not have a positive stop and therefore allow the screw to be rotated indefinitely. This is problematic because a surgeon may unknowingly overtighten the screw, or purposely overtighten the screw rather than face the risk of not tightening the screw enough. In either event, the bone thread will be damaged, compromising the integrity of the screw hole.

Another drawback in many designs is the need for separate components to center the bone screws in the passages and control the trajectory of each screw as it is driven through the spacer. Centering each screw in its respective bore hole or passage is important, particularly in designs having locking threads on the screw heads. External threads on screw heads must align and mate with the internal threads in the bore holes or passages when the screw heads enter the passages. This mating does not occur until the screw is almost completely inserted into the passage (i.e. when the head enters the passage). Because the passages are wider than the screw shanks, and because the screw shanks are not engaged with any part of the spacer, there is play that allows the screw to change alignment as it advances through the passage. To maintain proper screw alignment and trajectory, many designs, including some mentioned above, utilize a separate drill guide, guide pin or other implement to ensure that the screws remain centered in each hole. This adds additional steps to the procedure, and burdens the surgeon with additional components that must be handled during surgery.

Another drawback in many designs is that the spacer provides little support and stability to the screws. In U.S. Pub. No. 2008/0249575 and U.S. Pub. No. 2009/0030520, for example, only a small section of the screw head engages the inside passage of the spacer. The screw head represents a relatively small portion of the screw's length. Most of the screw extends through the passage and does not engage the spacer at all, allowing the screw shank to move laterally or polyaxially in the screw passage under load. As a result, the spacer contributes very little stability to the screw as it undergoes flexion/extension, medial/lateral bending and axial rotation.

Still another drawback in many designs is their need for a separate component, such as a cover plate or cover screw, placed over the anchors to inhibit the anchors from backing out of the implant. Implants that utilize detachable covers, like U.S. Pub. No. 2008/0249569, require the surgeon to handle additional instrumentation and components, and perform additional steps that can prolong surgery.

SUMMARY

The drawbacks of known interbody spacers are resolved to a large degree by Applicants' implant assemblies. In one embodiment, the assembly includes a bone screw having a hub portion and a shank portion. The shank portion includes a thread with a plurality of turns, the turns having a uniform diameter. The assembly also includes a spacer with an anterior end and a posterior end. The spacer forms at least one passage with a first section toward the anterior end for seating the hub portion of the screw and a second section toward the posterior end. The second section has a thread with a plurality of turns having a uniform diameter. The thread in the second section receives and mates with the thread of the bone screw.

In another embodiment, the assembly includes a bone screw having a hub portion and a shank portion. The hub portion includes a first locking mechanism and the shank portion includes a second locking mechanism. The second locking mechanism includes a thread having a plurality of turns, the turns having a uniform diameter. The embodiment also features a spacer having at least one passage for receiving the bone screw. The passage includes a first locking section and a second locking section. The first locking section is configured for mating engagement with the first locking mechanism of the hub portion of the bone screw. The second locking section includes a thread having a plurality of turns with a uniform diameter that receives and mates with the thread of the bone screw.

Another embodiment includes an anchor member and a spacer. The anchor member has a hub portion and a shank portion. The spacer forms at least one passage for receiving the anchor member. The passage has a first means for locking the anchor member in the passage against backout, and a second means for locking the anchor member in the passage against backout. The second means for locking the anchor member includes means for centering the anchor member in the passage and maintaining the anchor member centered in the passage as the anchor member is advanced through the passage.

BRIEF DESCRIPTION OF THE DRAWINGS

The embodiments that will be described will be better understood in conjunction with the drawing figures, of which.

DETAILED DESCRIPTION

Figure 1:
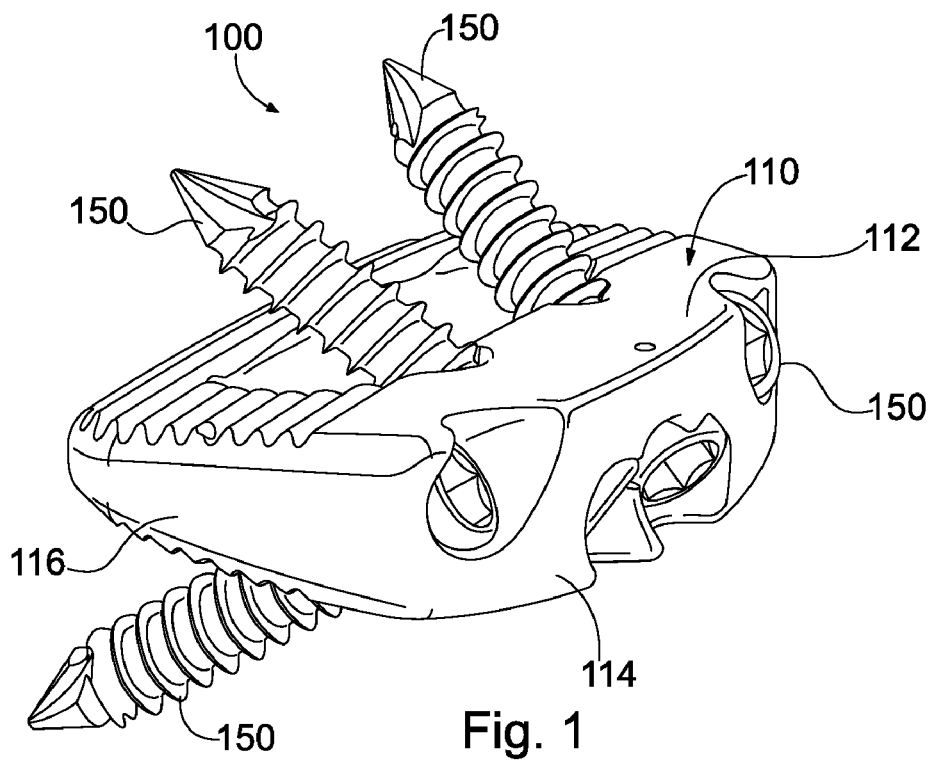
FIG. 1 is a perspective view of an implant assembly in accordance with one embodiment.
Figure 2:
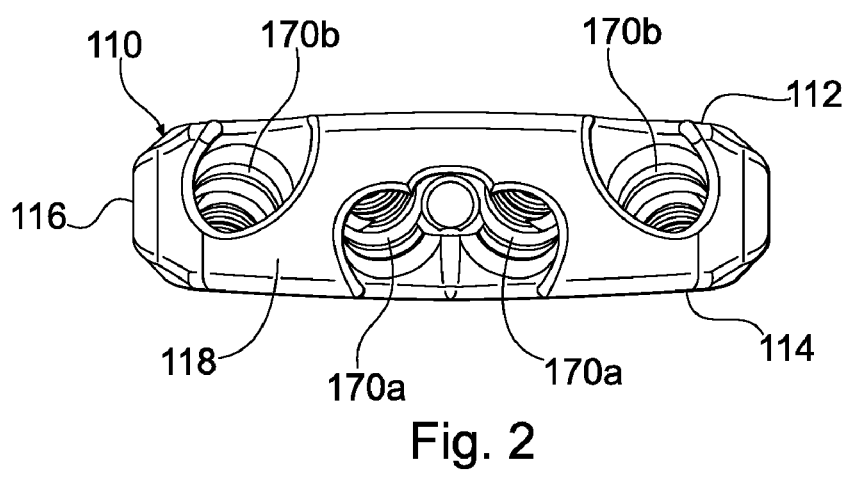
FIG. 2 is a front view of a component of the implant assembly of FIG. 1.
Figure 3:
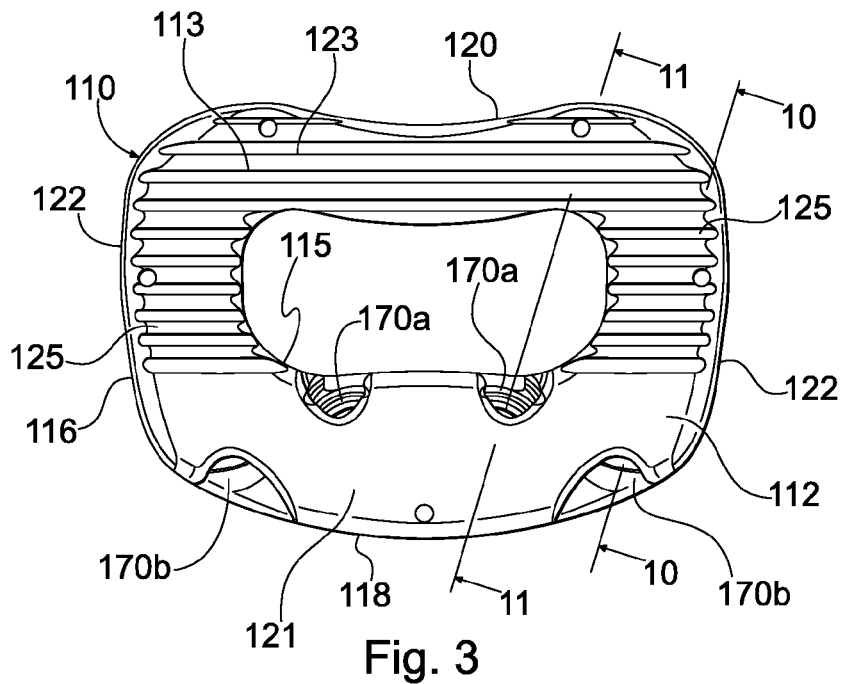
FIG. 3 is a top view of the component of FIG. 2.

Although the description is provided with reference to specific embodiments, the description is not intended to be limited to the details shown and described. Various modifications may be made in the details within the scope and range of equivalents of the claims.

Applicants' implant assemblies preferably feature a first locking mechanism for inhibiting backout of anchor elements, and a second locking mechanism for inhibiting backout of anchor elements. In addition to inhibiting backout, the second locking mechanism preferably provides a mechanical aid that performs a number of functions during different procedures or stages of operation. During insertion of an anchor element into the spacer, for example, the second locking mechanism may act as a centering mechanism that keeps the anchor element centered in the passage of the spacer and in alignment with a longitudinal axis of the passage as the anchor element is driven into bone. This eliminates the need for a separate centering guide. The second locking mechanism may also provide mechanical advantage by helping drive the anchor element into bone. This mechanical advantage reduces the need for pre-drilling pilot holes in the bone. The second locking mechanism may further provide mechanical advantage to assist in reversing the screw past the first locking mechanism in the event of a revision procedure or other event requiring removal of the anchor element. The first and second locking mechanisms are preferably arranged such that the second locking mechanism provides mechanical advantage to overcome or unlock the first locking mechanism, thereby allowing the screw to be removed from the spacer. The second locking mechanism may also provide additional stability to the anchor element as the anchor element receives loads during flexion/extension, medial/lateral bending or axial rotation.

In one embodiment, the implantable assembly includes a bone screw having a hub portion and a shank portion, the hub portion having a first locking mechanism and the shank portion having a second locking mechanism. The second locking mechanism includes a thread having a plurality of turns, the turns having a uniform diameter. The assembly also includes a spacer with an anterior end, a posterior end and a central opening to receive bone fusion material. The spacer includes at least one passage for receiving the bone screw, the passage having a first locking section and a second locking section. The first locking section is configured for mating engagement with the first locking mechanism of the hub portion of the bone screw. The second locking section has a thread comprising a plurality of turns having a uniform diameter adapted for receiving and mating with the thread of the bone screw.

The second locking section in the passage may be adapted to receive the second locking mechanism of the bone screw and maintain the bone screw in a centered axial position in the passage, where a longitudinal axis of the screw is coaxial with a longitudinal axis of the passage. The passage may include a proximal end at the anterior end of the spacer and a distal end that connects with the central opening, the thread of the second locking section starting at a midsection of the passage and ending at the distal end of the passage. The first locking mechanism may include a radially relieved recess around the hub portion of the screw, and the first locking section in the passage may include an annular rib. The rib may include an anterior side portion extending at an acute angle relative to a longitudinal axis of the passage, and a posterior side portion extending normal to the longitudinal axis of the passage. The first locking section may further include a seat portion having a larger diameter end and a smaller diameter end, the smaller diameter end adjoining the second locking section and forming a positive stop configured to limit advancement of the bone screw through the passage. Finally, the hub portion may feature a head located at a proximal end of the bone screw.

In another embodiment, an implantable assembly includes an anchor member and a spacer. The anchor member includes a hub portion and a shank portion. The spacer includes an anterior end, a posterior end, a central opening to receive bone fusion material, and at least one passage for receiving the anchor member. The passage includes a first means for locking the anchor member in the passage against backout, and a second means for locking the anchor member in the passage against backout. The second means for locking the anchor member includes means for centering the anchor member in the passage and maintaining the anchor member centered in the passage as the anchor member is advanced through the passage.

The passage includes a proximal end at the anterior end of the spacer and a distal end that connects with the central opening. The second means for locking the anchor member begins at a midsection of the passage and ends at the distal end of the passage. The anchor member may include a radially relieved recess around the hub portion of the screw. The first means for locking the anchor member in the passage against backout may include an annular rib extending around at least a portion of the perimeter of the passage. The rib has an anterior side portion extending at an acute angle relative to a longitudinal axis of the passage and a posterior side portion extending normal to the longitudinal axis of the passage. The first means for locking the anchor member in the passage against backout includes a seat portion having a larger diameter end and a smaller diameter end. The smaller diameter end adjoins the second means for locking the anchor member in the passage against backout. The first means for locking the anchor member in the passage against backout forms a positive stop that prevents further advancement of the hub portion through the passage. The shank portion of the anchor member includes a helical thread having a plurality of turns of uniform diameter. The second means for locking the anchor member in the passage against backout includes a helical groove in a wall of the passage. The helical groove includes a plurality of turns of uniform diameter that mate with the helical thread on the anchor member. The spacer includes an upper surface and a lower surface opposite the upper surface. The upper and lower surfaces converge toward one another toward the anterior end of the spacer. At least one of the upper surface and lower surface includes a plurality of ridges extending generally parallel to one another for engaging a vertebra. The spacer may include a first passage and a second passage, the first passage comprising a distal end contiguous with the upper surface, and the second passage comprising a distal end contiguous with the lower surface. The second means for locking the anchor member in the passage against backout may include means for axially displacing the anchor element toward the anterior end of the spacer and out of the passage in response to rotation of the anchor element.

Referring now to FIGS. 1-6, components of an exemplary implant assembly 100 are shown. Implant assembly 100 includes a spacer 110 configured to be inserted in a space between vertebral bodies that are to be fused. Spacer 110 includes an upper surface 112 and a lower surface 114 that are symmetrically arranged with respect to first axis $A_1$. A peripheral wall 116 extends between upper and lower surfaces 112 and 114. Peripheral wall 116 is characterized by a continuous surface made up of compound curvatures, including a number of convex curves and a concave curve that combine to create a generally rectangular shape. Peripheral wall 116 includes an anterior end 118, a posterior end 120, and a pair of sidewalls 122. Upper and lower surfaces 112 and 114 converge toward one another as they extend toward posterior end. A plurality of ridges 117 extend generally parallel to one another on each of the upper and lower surfaces 112 and 114. Ridges 117 define small grooves 119 between the ridges that enhance stability. In this arrangement, upper and lower surfaces 112 and 114 firmly engage endplates on vertebrae to secure spacer 110 between the vertebrae.

Figure 4:
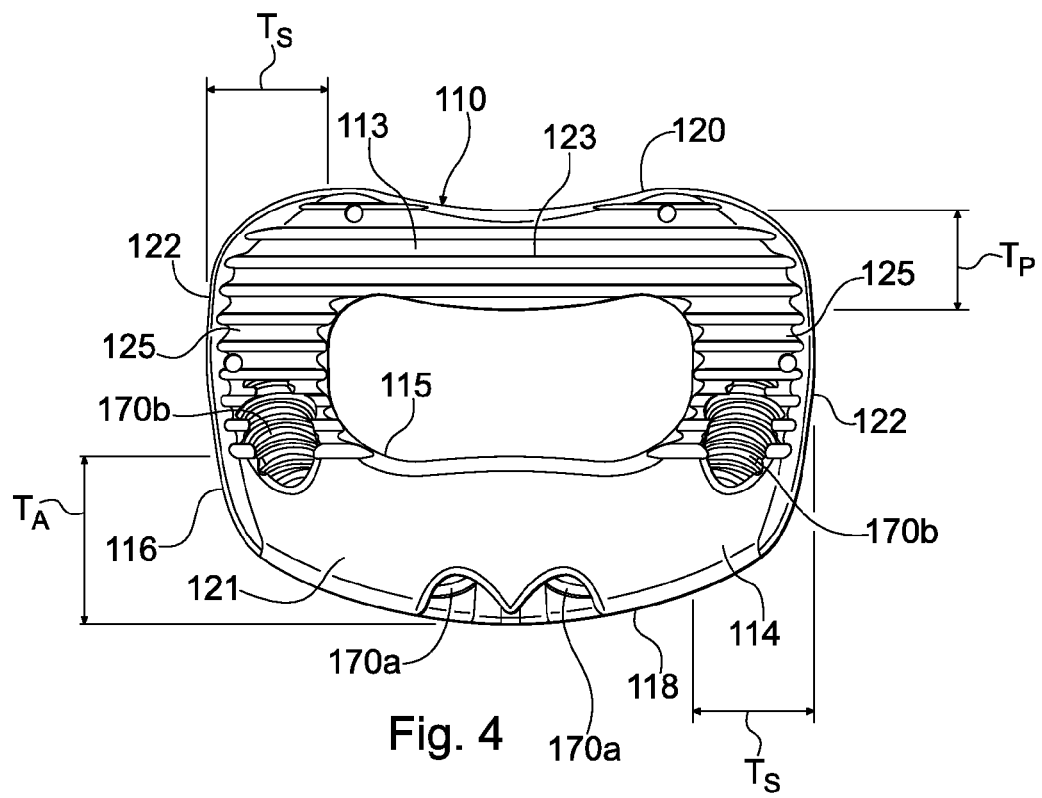
FIG. 4 is a bottom view of the component of FIG. 2.
Figure 5:
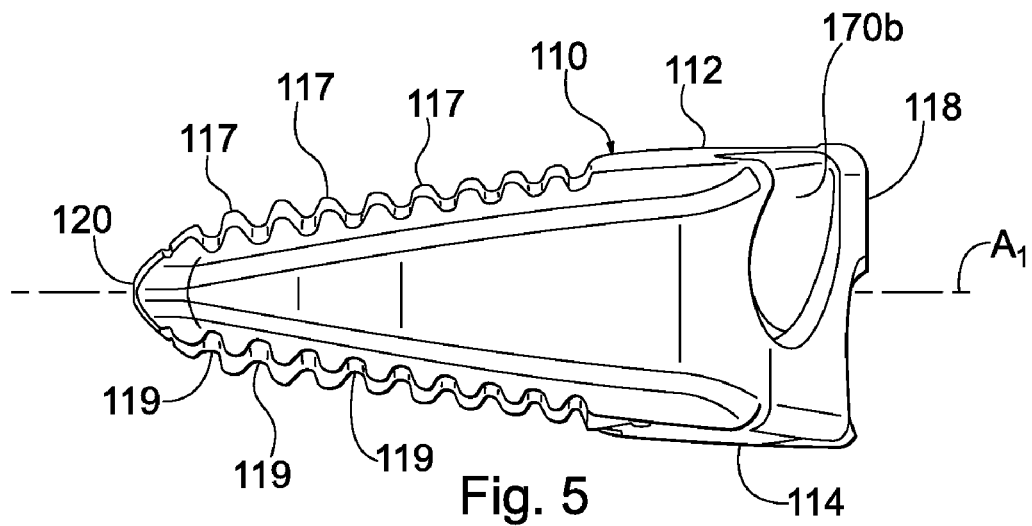
FIG. 5 is a left side view of the component of FIG. 2.
Figure 6:
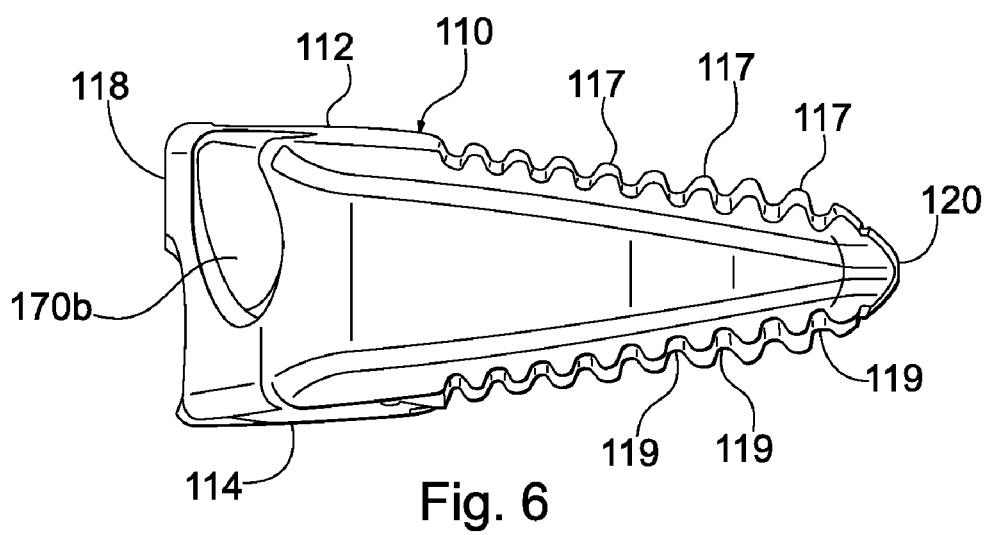
FIG. 6 is a right side view of the component of FIG. 2.
Figure 7:
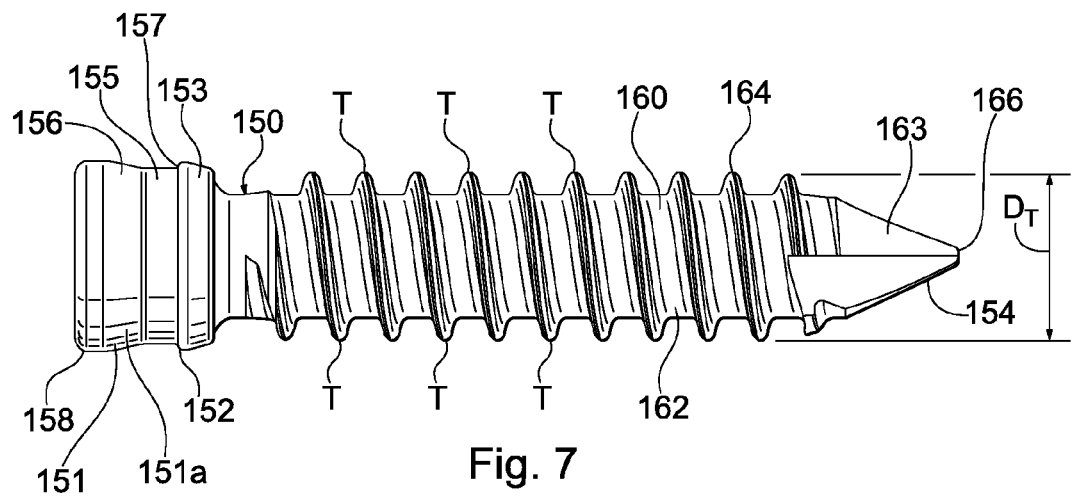
FIG. 7 is a side view of another component of the implant assembly of FIG. 1.
Figure 8:
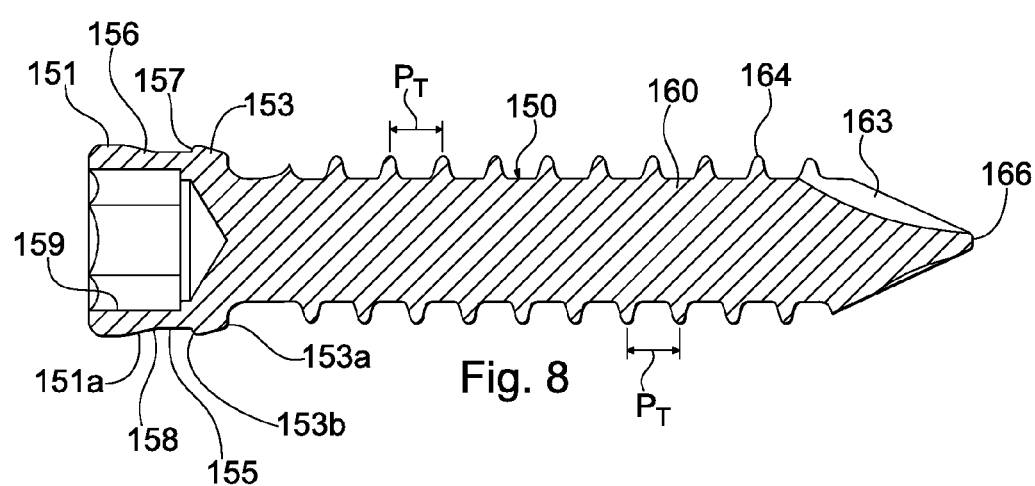
FIG. 8 is a side cross section view of the component of FIG. 7.
Figure 9:
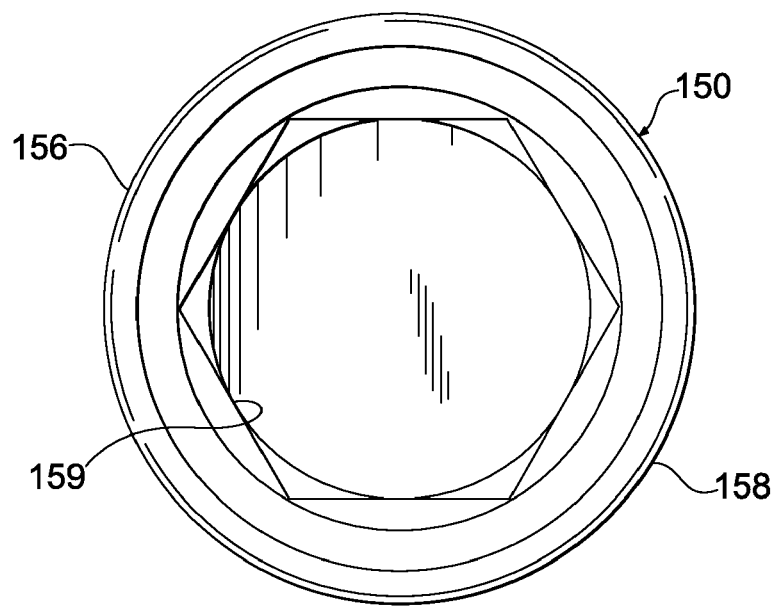
FIG. 9 is an end view of the component of FIG. 7.

Spacer 110 forms a ring like body 113 that surrounds a central opening 115. Central opening 115 is adapted to receive a bone fusion material, such as allograft or bone graft substitute to promote bonding and fusion of the spacer to the adjacent vertebrae. Body 113 includes an anterior body portion 121, a posterior body portion 123 and two side portions 125 that connect with one another to form the ring structure around central opening 115. Anterior body portion 121, posterior body portion 123 and side portions 125 are each characterized by a wall thickness $T_A$, $T_P$ and $T_S$, respectively, as shown in FIG. 4. For purposes of this description, the term "wall thickness" refers to the dimension across anterior body portion 121, posterior body portion 123 or side portions 125, as measured between the peripheral wall 116 and central opening 115, the lines of measurement located as shown in FIG. 4. Wall thickness $T_A$ is greater than wall thicknesses $T_P$ and $T_S$. As such, anterior body portion 121 has a greater wall thickness than the posterior body portion 123 and side portions 125. The significance of the wall thickness at anterior body portion 121 will be discussed in more detail below.

Applicants' implant assemblies can work with a number of different anchor members to secure the spacer in a vertebral space. Suitable anchor members include but are not limited to bone nails and bone screws. Preferred embodiments utilize bone screws with external threads, for reasons that will be described. Referring to FIGS. 1 and 7-9, implant assembly 100 includes four bone screws 150. Each bone screw 150 has a proximal end 152 and a distal end 154. Proximal end 152 includes a hub portion 156. Because of its location at the proximal end, hub portion 156 may be characterized as the screw's head 158. It will be understood, however, that the hub portion need not be located at the proximal end of the screw, and may be located at a midsection of the screw that is closer to the distal end. Head 158 is generally cylindrical and forms a socket 159 adapted to receive a driver or other tool to insert and remove screw 150 from a passage. Applicants' implant assemblies may include screw sockets with a variety of slot configurations for engagement with drivers and other instruments, including but not limited to flat head, Philips, Torx, or hexagonal slot configurations. In addition, Applicants' implant assemblies may include sockets with a variety of couplings for engagement with drivers and other instruments, including but not limited to internal threads, deformable detents or spring loaded pins. Socket 159 has a hexagonal shape adapted to receive a hexagonal driver tip, the hexagonal shape being shown best in FIG. 9.

Screw 150 further includes a shank portion 160. Shank portion 160 is characterized by an elongated cylindrical body portion 162 of constant diameter, and a conical tip portion 163. Tip portion 163 adjoins body portion 162 and converges to a pointed tip 166. Body portion 162 includes an external thread 164 having a plurality of turns T. The term "turn" is intended to mean a section of a thread that passes through an angle of 360° (i.e. makes one 360° rotation) around body portion 162. Thread 164 has a uniform pitch $P_T$. The term "pitch" is intended to mean the axial distance or length of each turn T. Thread 164 also has a uniform diameter $D_T$.

As noted above, Applicants' spacers preferably have an enlarged wall thickness at the anterior body portion, as compared to the posterior body portion and side portions. The enlarged wall thickness allows for longer passages through the anterior body portion, with lengths and dimensions that permit the passages to engage anchor members at multiple sections. The passages are sufficiently long to engage both the hub portion and the shank portion of anchor members so as to facilitate multiple locking points against backout. Because the longer passages engage a substantial portion of the anchor member, the passages can also provide mechanical advantage and support that assists with centering the screw, driving the screw into bone, removing the screw from bone, and stabilizing the screw relative to the spacer during periods of flexion/extension, medial/lateral bending, and axial rotation.

Spacer 110 has four passages adapted to receive bone screws 150. For purposes of this description, the four passages may be differentiated in terms of their relative positions in FIGS. 2-4, which show two interior passages 170a shown near the center of the spacer, and two exterior passages 170b shown toward the side portions of the spacer. Interior passages 170a begin at anterior end 118 contiguous with lower surface 114 and extend to upper surface 112 where they exit through anterior body portion 121. Exterior passages 170b begin at anterior end 118 contiguous with upper surface 112 and extend to lower surface 114 where they exit through side portions 125 of body 113. Wall thickness $T_A$ provides interior passages 170a with axial lengths sufficient to engage a bone screw 150 at both the head portion 158 and shank portion 160. Exterior passages 170b have even greater axial lengths because they extend through anterior body portion 121 and into side portions 125. As such, outer passages 170b also have sufficient lengths to engage a bone screw 150 at both head portion 158 and shank portion 160.

Applicants' implant assemblies may include dual locking mechanisms that inhibit backout of screws. The dual locking mechanisms may include a first locking feature that acts on the hub portion of the anchor element, and a second locking feature that acts on the shank portion of the anchor element. In preferred assemblies, the second locking feature is more than just a redundant locking mechanism that inhibits movement of the screw. As will be described, the second locking feature preferably serves as: (1) a means for centering the anchor member as it is inserted through the passage, (2) a means for unlocking the first locking feature when the anchor member is to be removed from the passage, (3) a means for stabilizing the anchor member in the passage when the anchor member is under load, and (4) a means for providing a positive stop that signals when the anchor member is completely advanced, preventing a surgeon from overtightening the anchor member.

In implant assembly 100, the first locking feature is provided in part by engagement surfaces on screw head 158. Head 158 includes a crown portion 151 and a seat portion 153 that have maximum diameters exceeding the diameter $D_T$ of thread 164. Crown portion 151 and seat portion 153 are separated by a radially relieved section between the crown portion and seat portion, forming an annular groove 155. Seat portion 153 has a conical shape, with a leading edge 153a having a first diameter and a trailing edge 153b with a second diameter larger than the first diameter. The diameter at trailing edge 153b gradually tapers down to a smaller diameter at leading edge 153a. Trailing edge 153b forms a lip 157 adjacent to groove 155. Crown portion 151 has a leading edge 151a with a spherical profile.

Figure 10:
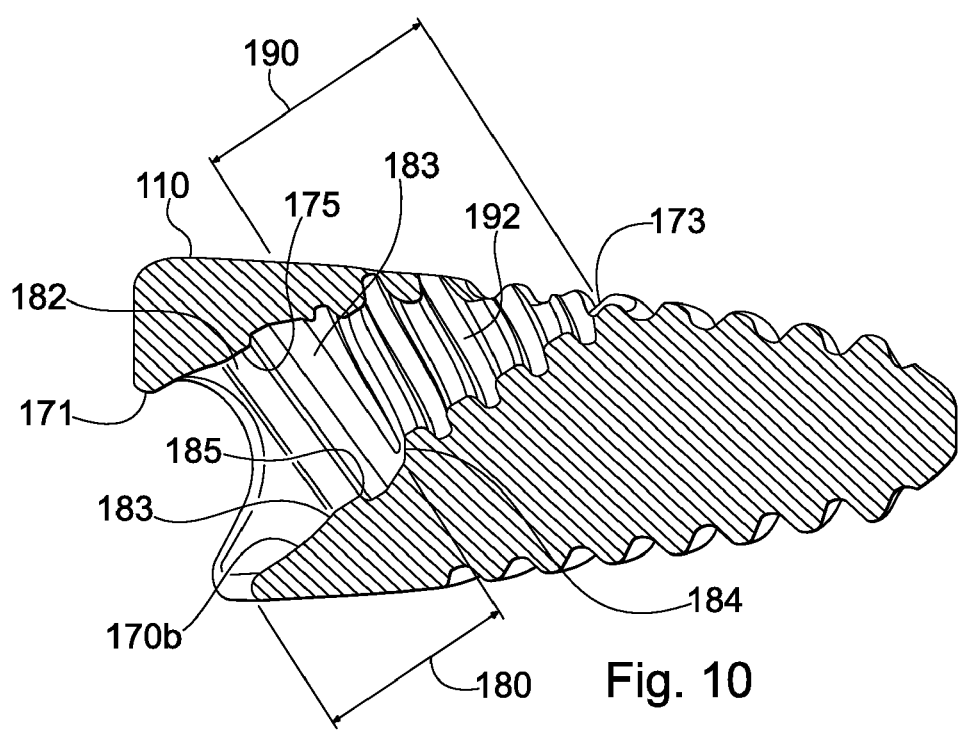
FIG. 10 is a side cross section view of the component of FIG. 2 taken through line 10-10 in FIG. 3.

The first locking feature is also provided in part by first locking sections 180 in passages 170a and 170b. Referring to FIG. 10, an exemplary first locking section 180 is shown in passage 170b. The first locking sections 180 are similarly configured in each of the passages in spacer 110. Therefore, the first locking sections 180 shown in FIGS. 10 and 11 will be described with the understanding that the first locking sections in the other passages are similarly arranged. In FIG. 10, first locking section 180 is located toward a proximal end 171 of passage 170b and has an annular rib 182 that extends radially inwardly into the passage. Rib 182 defines a constriction in passage 170b, forming an opening 175 that is smaller than adjacent sections of first locking section 180. The diameter of opening 175 is greater than the diameter of any section on shank portion 160, allowing passage of the shank portion without any interference. Moreover, the diameter of opening 175 is equal to or slightly greater than the diameter of screw head 158 at groove 150, but less than the maximum diameter of crown portion 151 and less than the diameter of seat portion 153 at both the leading edge 153a and trailing edge 153b.

As a result, rib 182 is configured to contact leading edge 153a of seat portion 153 as the screw is inserted into passage 170b.

Figure 11:
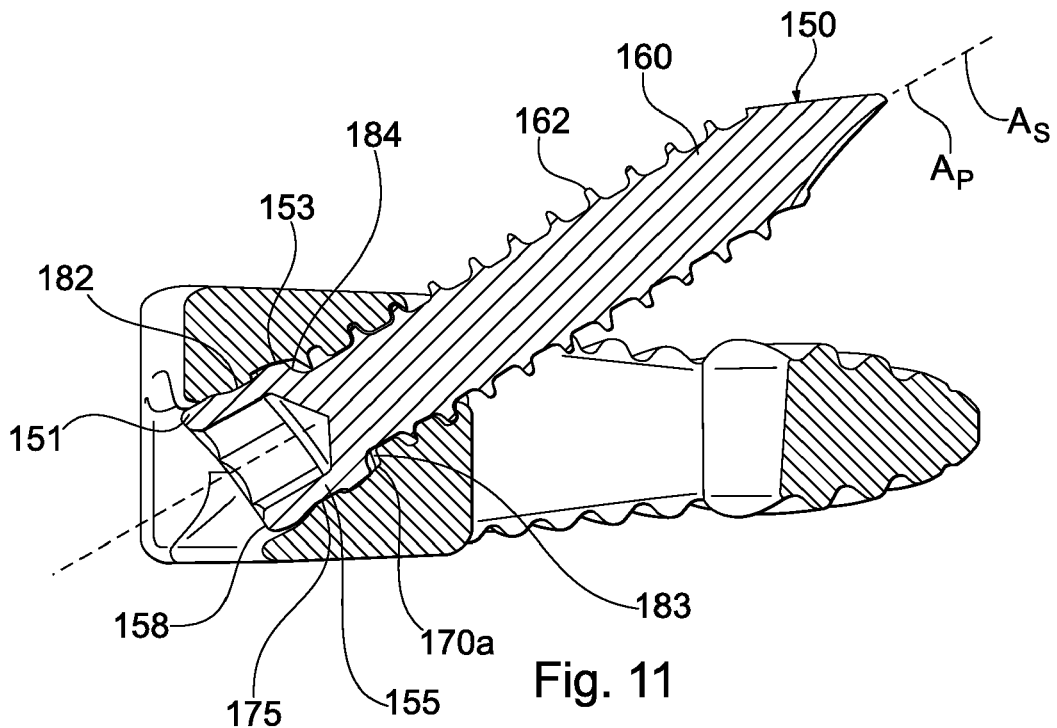
FIG. 11 is a side cross section view of the component of FIG. 2 taken through line 11-11 in FIG. 3, with the component of FIG. 7 inserted in the passage.

Rib 182 is deformable in response to contact with seat portion 153 of screw head 158. In particular, rib 182 is deformable between a relaxed state, in which opening 175 has a first size, and a deflected state, in which opening 175 is dilated or stretched to a second size that is greater than the first size of the opening in the relaxed state. In this configuration, rib 182 is allows passage of the screw shank 160 without interference but contacts seat portion 150. Upon contact with leading edge 153a of seat portion 150, rib 182 deflects outwardly to stretch the size of opening 175 until the opening is large enough for the entire seat portion to pass through the rib. After the entire seat portion 153 passes through rib 182, the rib is positioned in groove 155, where there is more clearance that allows the rib to return to its relaxed configuration, or partially return to its relaxed configuration, depending on the rib's material and its degree of elasticity or plasticity. The diameter of crown portion 151 is larger than opening 175 after seat portion 153 penetrates through rib 182. As a result, rib 182 remains captured within groove 155 between crown portion 151 and seat portion 153. FIG. 11 shows a screw 150 in a captured or locked state in passage 170a. Leading edge 153a of seat portion 153 is positioned in proximity to a seat portion 184 in the passage. Seat portion 184 creates a constriction in passage 170b that prevents screw 150 from advancing any further through the passage.

Rib 182 has a ramp 183 at one end that is oriented toward the proximal end 171 of passage 170b. Ramp 183 is oriented at an acute angle with respect to the axis of passage 170b, providing a gradual change in the size of the passage. Rib 182 also has a steep ledge 185 that is oriented toward a distal end 173 of passage 170b. Ramp 183 is configured to facilitate relatively unhindered passage of seat portion 153 in a distal direction over rib 182 as head 158 is inserted into first locking section 180. In contrast, ledge 185 is configured to provide an abrupt hindrance or blockage against movement of head 158 out of the first locking section 180. Ledge 185 is configured to abut lip 157 on screw head to inhibit seat portion 153 from reversing or backing out past the rib. In this arrangement, the engagement of lip 157 with ledge 185 inhibits the screw head from backing out of passage 170b until there is sufficient axial force to push the screw back out past rib 182. Rib 182 and ledge 185 provide sufficient interference to withstand axial forces and retain the screw against back out when the implant is in use. Nevertheless, rib 182 and ledge 175 are also adapted to yield once axial force on the screw reaches a threshold limit. This threshold limit or "unlocking force" exceeds the maximum expected axial force exerted on the screw under load. The unlocking force can be reached by applying a sufficient amount of torque on the screw. The torque required to reach the unlocking force and reverse the seat portion 153 past rib 182 during removal is dependent on a number of variables, including but not limited to the geometry and dimensions of the screw head, rib and passage. In general, the torque required to reach the unlocking force and reverse the seat portion 153 past rib 182 during removal is more than the torque required to advance the seat portion past rib during insertion of the screw. This difference is due to the geometry of rib 182 which, as noted above, facilitates passage of seat portion 153 during insertion of screw 100 into the passage, but provides more resistance to removal of the screw from the passage. In a preferred embodiment, the amount of torque required to remove the screw past the rib (removal torque) is approximately twice the amount of torque required to insert the screw past the rib (insertion torque). The ratio of removal torque to insertion torque may be lower or higher, however, and still provide acceptable performance.

Applicants' preferred assemblies incorporate one or more mechanisms that provide sensory feedback to alert the surgeon when the first locking mechanism is engaged, when the anchor member is completely driven into place, and when the first locking mechanism is unlocked. First locking section 180, for example, includes a small chamber 183 beyond rib 182. Chamber 183 provides sufficient volume to receive seat portion 153 after the seat portion passes through rib 182, plus an additional amount of space that allows the seat portion and screw to advance a little further in the passage. In this configuration, screw 150 is subject to resistance force from the interference that occurs as seat portion 153 engages rib 182. This resistance force is abruptly removed the moment seat portion 153 passes completely through rib 182. The change in resistance provides tactile feedback that is instantly felt by the surgeon, signaling to the surgeon when the first locking mechanism is engaged. The same change of resistance is detected when the screw is being unscrewed, to alert the surgeon when the first locking mechanism is unlocked, and when the screw is released. In either instance of locking or unlocking, rib 182 preferably provides an audible click in conjunction with the tactile feedback to confirm when the first locking feature is locked or unlocked.

Once screw 150 is driven through rib 182 into the locked position, the screw is driven further until leading edge 153a of seat portion 153 bottoms out against seat portion 184 in the passage. Contact between seat portions 153 and 184, in conjunction with the second locking features to be described below, provides a second resistance force or positive stop that alerts the surgeon when the screw is fully driven into place. This tactile feedback signals when the screw is fully inserted into spacer 110, and is important to prevent the surgeon from overtightening the screw. Overtightening the screw can possibly damage the threads established in the bone.

As noted above, Applicants' preferred assemblies have second locking features that act on the shank portions of anchor elements. In the embodiment of FIG. 10, the second locking feature is provided in part by a second locking section 190 in each passage 170a and 170b. Like the first locking section 180, second locking section 190 has the same general configuration in each passage, except that the axial length of the second locking section is longer in exterior passages 170b than in interior passages 170a. Second locking sections 190 include internal threads 192 that engage the external threads 164 on bone screws 150. In contrast to many known spacers, spacer 110 does not permit polyaxial motion of screws within passages 170a and 170b, much less allow the shank to deviate from the central axis in each passage. As shown in FIG. 11, second locking section 190, and particularly the engagement of threads 164 and 192, keep the screw shank's longitudinal axis $A_S$ coaxial with the longitudinal axis $A_P$ of passage 170a.

Second locking section 190 provides a number of advantages. As an initial matter, second locking section 190 provides a second locking mechanism that inhibits backout. Internal thread 190 creates a radial obstruction with thread 164 that limits movement of the screw within passage 170a. Screw 150 cannot translate in passage 170a unless it is rotated on its axis, with sufficient torque to overcome frictional resistance between the screw and passage wall.

Second locking section 190 also provides a means for centering the anchor member as it is inserted through the passage and keeps the screw centered during its advancement through spacer 110 into the bone. The axial trajectory of the screw 150 is controlled by threads 164 and 192 as the screw is driven into the bone. This eliminates the need for handling and using a separate guide plate, template, or other component to control the axial position of the screw in the passage during insertion.

Second locking section 190 further provides mechanical advantage that works in two ways. The engagement of threads 164 and 192 provide additional leverage or push as the screw is rotated clockwise and driven into bone. This engagement of threads 164 and 192 occurs before tip 166 of screw 160 contacts the bone. The increased leverage makes it easier to drive the screw into the bone, which in turn makes it possible to use self-tapping screws and avoid drilling pilot holes. The engagement of threads 164 and 192 also provides additional leverage or push in the reverse direction when the screw is rotated counterclockwise. The additional leverage can be used, for example, to help remove the screw out of the passage during a revision procedure. Specifically, the engagement of threads 164 and 192 provide sufficient force to push seat portion 153 of screw head 158 back over rib 182, thereby overcoming and unlocking the first locking mechanism. Threads 164 and 192 take up much of the stress during the unlocking step, thereby relieving stress on the thread in the bone, and reducing or eliminating the potential for stripping the bone thread.

Moreover, second locking section provides a means for stabilizing the anchor member in the passage when the anchor member is under load. Unlike many prior spacers which provide room for the bone screw to move within the passage under load, spacer 110 engages the shank of the bone screw in a constrained manner, greatly reducing micro motion that can loosen the screw over time.

Lastly, second locking mechanism provides a positive stop in conjunction with seat portions 153 and 184 that signals when screw 160 is completely tightened. This provides tactile feedback that alerts the surgeon when he or she should stop tightening the screw, and prevents the bone thread from getting stripped.

Figure 12:
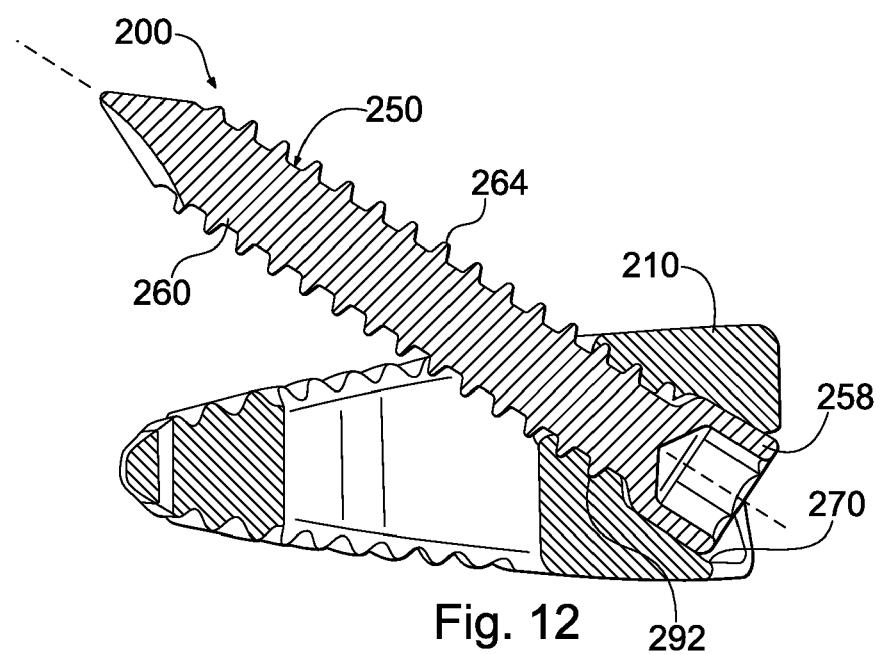
FIG. 12 is a side cross section view of an implant assembly in accordance with another embodiment.

Referring now to FIG. 12, another exemplary implant assembly 200 is shown. Assembly 200 is similar in many respects to assembly 100, but features only one type of locking mechanism. In particular, assembly 200 includes a spacer 210 with four passages 270, one of the passages being shown. Assembly 200 also includes four bone screws 250, each screw having a head portion 258 and shank portion 260 with an external thread 264. Passages 270 have substantially identical configurations and extend through spacer 210 in the same arrangement that passages 170a and 170b extend in FIGS. 1 and 2. Unlike passages 170a and 170b, passages 270 have no rib or other mechanism in the first section of the passage to engage the head portions 258 of screws 250. Also, the screw heads 258 do not feature grooves. Spacer 210 only has internal threads 292 in the distal or second section of each passage 270, much like the internal threads 192 in assembly 100. Threads 292 are positioned to mate with the external threads 264 on screws 250. In this arrangement, threads 292 engage the external threads 264 on screws 250 to inhibit backout of the screws. In addition, threads 292 provide means for keeping the screws 250 centered in passages 270 while the screws are advanced through the spacer. Threads 292 also provide a mechanical advantage that makes it easier to drive the screws into bone. Moreover, threads 292 provide means for stabilizing screws 250 in passages 270 when the screws are under load. Finally, threads 292 provide a positive stop that prevents advancement of screws past a certain point in passage 270, alerting the surgeon as to when the screw is fully advanced so the surgeon can avoid overtightening the screw.

Applicants' implant assemblies may be formed in whole or in part from a variety of biocompatible materials. Examples of suitable materials include, but are not limited to, stainless steel, ceramics, polymers, polymer composites, PEEK, PEEK composites, shape memory alloys, titanium, titanium alloys, cobalt chrome alloys, or any combinations of these materials. Rib 182, for example, is preferably formed of a deformable material such as PEEK, which allows the rib to deform in response to contact with the screw head 158, but deflect back toward its relaxed state to lock the screw head in the first locking section.

While a limited number of embodiments have been shown and described herein, it will be understood that the illustrated embodiments are provided by way of example only. Numerous variations, changes and substitutions will occur to those skilled in the art without departing from the scope of this disclosure and the claims. For example, in those assemblies that feature a first locking mechanism and first locking section, the first locking section may include a variety of elements other than ribs for inhibiting backout. The first locking mechanism may be a plurality of deformable tabs, for example, that circumscribe the passage in positions to engage the anchor elements at one or more points along the hub portion or head portion, as the case may be. In this alternative arrangement, the tabs may be located in a ring configuration at one axial location with the first locking section of the passage, or may be arranged in sets that are axially offset from one another in the first locking section to engage different sections of the hub portion or head portion. As with rib 182, the tabs are configured to yield in response to a threshold force that allows insertion of the anchor element in one direction into a locked condition, and withdrawal of the anchor element in the opposite direction into an unlocked condition.

Alternatively, the first locking mechanism may be a plurality of collapsible petals on the hub or head portion of the screw, such as those shown in applicant's U.S. application Ser. No. 11/732,752, published under U.S. Pub. No. 2007/0288025 A1, the contents of said application being incorporated by reference herein in its entirety and for all purposes. The petals may be designed to collapse during insertion and radially expand within the first locking section to secure the hub or head portion, and inhibit backout. The first locking section in the passage may include a rigid locking projection, such as a tab or annular ring extending from the passage wall. The petals are formed with rounded or tapered leading and trailing edges to allow them to collapse toward one another as they pass through the rigid locking projection in the first locking section.

Applicants' implant assemblies may also feature fewer than four anchor elements, or more than four anchor elements. In such cases, the anchor elements and passages may be symmetrically arranged similar to the embodiment shown in FIG. 1, with equal or unequal numbers of anchor elements extending into the superior vertebra and inferior vertebra. Accordingly, it is intended that the appended claims cover all such variations as fall within the scope of this disclosure.

What is claimed:

1. An implantable assembly comprising:
a bone screw having a hub portion and a shank portion, the hub portion comprising a first locking mechanism and the shank portion comprising a second locking mechanism, the second locking mechanism comprising a thread having a plurality of turns, the turns having a uniform diameter; and
a spacer comprising an anterior end, a posterior end and a central opening to receive bone fusion material, the spacer forming at least one passage for receiving the bone screw, the passage comprising a first locking section and a second locking section, the second locking section having a thread comprising a plurality of turns having a uniform diameter,
wherein the first locking section of the passage is engaged with the first locking mechanism of the hub portion of the bone screw, and wherein the thread of the second locking section in the spacer is engaged with the thread of the second locking mechanism of the bone screw.

2. The implantable assembly of claim 1, wherein the second locking section in the passage is adapted to receive the second locking mechanism of the bone screw and maintain the bone screw in a centered axial position in the passage in which a longitudinal axis of the screw is coaxial with a longitudinal axis of the passage.

3. The implantable assembly of claim 1, wherein the passage comprises a proximal end at the anterior end of the spacer and a distal end that connects with the central opening, the thread of the second locking section starting at a midsection of the passage and ending at the distal end of the passage.

4. The implantable assembly of claim 1, wherein the first locking mechanism comprises a radially relieved recess around the hub portion of the screw, and the first locking section comprises an annular rib extending around at least a portion of the perimeter of the passage.

5. The implantable assembly of claim 4, wherein the rib comprises an anterior side portion extending at an acute angle relative to a longitudinal axis of the passage and a posterior side portion extending normal to the longitudinal axis of the passage.

6. The implantable assembly of claim 1, wherein the first locking section in the passage comprises a seat portion that is adjacent to the second locking section in the passage, the seat portion forming a positive stop configured to prevent the hub portion from advancing past the seat portion.

7. The implantable assembly of claim 1, wherein the hub portion comprises a head located at a proximal end of the bone screw.

8. An implantable assembly comprising:
an anchor member having a hub portion and a shank portion; and
a spacer comprising an anterior end, a posterior end and a central opening to receive bone fusion material, the spacer forming at least one passage for receiving the anchor member, the passage comprising a first means for locking the anchor member in the passage against backout, and a second means for locking the anchor member in the passage against backout, the second means for locking the anchor member against backout comprising means for centering the anchor member in the passage and maintaining the anchor member centered in the passage as the anchor member is advanced through the passage,
wherein the first means for locking the anchor member in the passage against backout is engaged with the hub portion of the anchor member, and
wherein the second means for locking the anchor member in the passage against backout is engaged with the shank portion of the anchor member.

9. The implantable assembly of claim 8, wherein the passage comprises a proximal end at the anterior end of the spacer and a distal end that connects with the central opening, the second means for locking the anchor member against backout starting at a midsection of the passage and ending at the distal end of the passage.

10. The implantable assembly of claim 8, wherein the anchor member comprises a radially relieved recess around the hub portion of the screw, and the first means for locking the anchor member in the passage against backout comprises an annular rib extending around at least a portion of the perimeter of the passage.

11. The implantable assembly of claim 10, wherein the rib comprises an anterior side portion extending at an acute angle relative to a longitudinal axis of the passage and a posterior side portion extending normal to the longitudinal axis of the passage.

12. The implantable assembly of claim 8, wherein the first means for locking the anchor member in the passage against backout comprises a seat portion that is adjacent to the second means for locking the anchor member in the passage against backout.

13. The implantable assembly of claim 8, wherein the first means for locking the anchor member in the passage against backout forms a positive stop configured to prevent further advancement of the hub portion through the passage.

14. The implantable assembly of claim 8, wherein the hub portion comprises a head located at a proximal end of the anchor member.

15. The implantable assembly of claim 8, wherein the shank portion of the anchor member comprises a helical thread having a plurality of turns of uniform diameter, and the second means for locking the anchor member in the passage against backout comprises a helical groove in a wall of the passage, the helical groove having a plurality of turns of uniform diameter that mate with said plurality of turns of the helical thread on the anchor member.

16. The implantable assembly of claim 8, wherein the spacer comprises an upper surface and a lower surface opposite the upper surface, the upper and lower surfaces converging toward one another toward the posterior end of the spacer.

17. The implantable assembly of claim 16, wherein at least one of the upper surface and lower surface comprises a plurality of ridges extending generally parallel to one another for engaging a vertebra.

18. The implantable assembly of claim 16, wherein the at least one passage comprises a first passage and a second passage, the first passage comprising a distal end contiguous with the upper surface, and the second passage comprising a distal end contiguous with the lower surface.

19. The implantable assembly of claim 8, wherein the second means for locking the anchor member in the passage against backout comprises means for axially displacing the anchor member toward the anterior end of the spacer and out of the passage in response to rotation of the anchor element.

20. An implantable assembly comprising:
a bone screw having a hub portion and a shank portion, the shank portion comprising a thread with a plurality of turns, the turns having a uniform diameter; and
a spacer comprising an anterior end and a posterior end, the spacer forming at least one passage, the passage comprising a first section toward the anterior end for seating the hub portion of the screw and a second section toward the posterior end, the first section having an engagement section for trapping a portion of the hub portion in the passage and preventing the hub portion from backing out of the passage, the second section having a thread comprising a plurality of turns having a uniform diameter adapted for receiving and mating with the thread of the bone screw,
wherein the engagement section of the first section of the passage is engaged with the hub portion, trapping the hub portion in the passage, and
wherein the thread of the second section of the passage is mated with the thread of the bone screw.

* * * * *